(12) United States Patent
Loscalzo et al.

(10) Patent No.: US 7,556,824 B2
(45) Date of Patent: Jul. 7, 2009

(54) TRANSDERMAL PATCH COMPOSITION FOR TREATING VASCULAR DISEASES CHARACTERIZED BY NITRIC OXIDE INSUFFICIENCY

(75) Inventors: Joseph Loscalzo, Dover, MA (US); Joseph A. Vita, Hingham, MA (US); Michael D. Loberg, Boston, MA (US); Manuel Worcel, Boston, MA (US)

(73) Assignee: NitroMed, Inc., Charlotte, NC (US)

( * ) Notice: Subject to any disclaimer, the term of this patent is extended or adjusted under 35 U.S.C. 154(b) by 644 days.

(21) Appl. No.: 10/679,257

(22) Filed: Oct. 7, 2003

(65) Prior Publication Data

US 2004/0071766 A1   Apr. 15, 2004

Related U.S. Application Data

(62) Division of application No. 09/697,317, filed on Oct. 27, 2000, now Pat. No. 6,635,273.

(60) Provisional application No. 60/179,020, filed on Jan. 31, 2000, provisional application No. 60/162,230, filed on Oct. 29, 1999.

(51) Int. Cl.
*A61F 13/00* (2006.01)
*A61K 9/70* (2006.01)
*A61L 15/12* (2006.01)
*A61L 15/44* (2006.01)

(52) U.S. Cl. ...................................... 424/449; 424/447
(58) Field of Classification Search .................. 424/449, 424/447
See application file for complete search history.

(56) References Cited

U.S. PATENT DOCUMENTS

| 4,293,565 | A | | 10/1981 | Cordes et al. |
| 4,584,315 | A | | 4/1986 | Marshall |
| 4,828,836 | A | | 5/1989 | Elger et al. |
| 4,868,179 | A | * | 9/1989 | Cohn .......................... 514/248 |
| 5,593,694 | A | | 1/1997 | Hayashida et al. |
| 5,627,191 | A | * | 5/1997 | Birch et al. .................. 514/303 |
| 5,645,839 | A | * | 7/1997 | Chobanian et al. .......... 424/400 |
| 5,668,117 | A | * | 9/1997 | Shapiro ........................ 514/55 |
| 5,760,069 | A | | 6/1998 | Lukas-Laskey et al. |
| 5,837,289 | A | | 11/1998 | Grasela et al. |
| 5,853,751 | A | | 12/1998 | Masiz |
| 5,891,459 | A | | 4/1999 | Cooke et al. |
| 5,902,821 | A | | 5/1999 | Lukas-Laskey et al. |
| 5,968,983 | A | | 10/1999 | Kaesemeyer et al. |
| 5,973,011 | A | | 10/1999 | Noack et al. |
| 6,103,769 | A | | 8/2000 | Kelm |
| 6,117,872 | A | | 9/2000 | Maxwell et al. |
| 6,242,432 | B1 | | 6/2001 | del Soldato |
| 6,319,515 | B1 | | 11/2001 | Hidaka et al. |
| 6,458,797 | B1 | | 10/2002 | Adams et al. |
| 6,465,463 | B1 | | 10/2002 | Cohn et al. |
| 6,635,273 | B1 | | 10/2003 | Loscalzo et al. |
| 2004/0005306 | A1 | | 1/2004 | Loscalzo et al. |
| 2004/0063719 | A1 | | 4/2004 | Adams et al. |

FOREIGN PATENT DOCUMENTS

| EP | 0327263 A | 8/1989 |
| EP | 0 968 713 A1 | 5/1998 |
| JP | 09059152 | 3/1997 |
| WO | WO 95/26725 | 10/1995 |
| WO | WO 98/21193 | 5/1998 |
| WO | WO 99/00361 | 1/1999 |
| WO | WO 99/66921 | 12/1999 |
| WO | WO 99/67231 | 12/1999 |
| WO | WO 01/35961 A | 5/2001 |

OTHER PUBLICATIONS

Klemsdal et al. 1994. A New Isosorbide Dinitrate Extended-Release Formulation: Pharmacokinetic and Clinical Parameters in Patients with Stable Angina Pectoris. Eur. J. Clin. Pharmacol., 47:351-354.*
Wikipedia, Anonymous, Isosorbide mononitrate. From Wikipedia pp. 1-4 Printed Oct. 18, 2007.*
Franciosa et al, Circulation, 59(6):1085-1091(1979).
Lanas et al, Rev. Med. Chile, 107:926-930(1979).
Usdin et al, Coeur, 10(1):119-128(1979).
Jun. 21, 2004. Supplementary Partial European Search Report for EP 00 97 6651.0.
Franciosa, Joseph A., "African-American Heart Failure Trial (A-HeFT): Rationale, Design, and Methodology," Journal of Cardiac Failure, vol. 8, No. 3, 2002, pp. 128-135.
Yancy, Clyde W., et al., "Race and the Response to Adrenergic Blockage with Carvedilol in Patients with Chronic Heart Failure," N. Engl. J. Med., vol. 344, No. 18, May 3, 2001, pp. 1358-1365.

(Continued)

*Primary Examiner*—Jon P Weber
*Assistant Examiner*—Kailash C Srivastava
(74) *Attorney, Agent, or Firm*—Wilmer Cutler Pickering Hale and Dorr LLP

(57) ABSTRACT

The present invention provides novel transdermal patch comprising a therapeutic amount of a hydralazine compound and at least one of isosorbide dinitrate and isosorbide mononitrate in therapeutically effective dosage of each of the aforementioned compounds.

8 Claims, 3 Drawing Sheets

OTHER PUBLICATIONS

Yancy, Clyde W., "Heart Failure in African Americans: A Cardiovascular Enigma," Journal of Cardiac Failure, vol. 6, No. 3, 2000, pp. 183-186.
Exner, Derek V., et al., "Lesser Response to Angiotensin-Converting-Enzyme Inhibitor Therapy in Black as Compared with White Patients with Left Ventricular Dysfunction," N. Engl. J. Med., vol. 344, No. 18, May 3, 2001, pp. 1351-1357.
Packer, Milton, et al., "Effect of Carvedilol on Survival in Severe Chronic Heart Failure," N. Engl. J. Med., vol. 344, No. 22, May 31, 2001, pp. 1651-1658.
"A Trial of the Beta-Blocker Bucindolol in Patients with Advanced Chronic Heart Failure," N. Engl. J. Med., vol. 344, No. 22, May 31, 2001, pp. 1659-1667.
Braunwald, Eugene, "Expanding Indications for Beta-Blockers in Heart Failure," N. Engl. J. Med., vol. 344, No. 22, May 31, 2001, pp. 1711-1712.
Schwartz, Robert S., "Racial Profiling in Medical Research," N. Engl. J. Med., vol. 344, No. 18, May 3, 2001, pp. 1392-1393.
Levine, T. Barry, "Paradoxical Hypertension after Reversal of Heart Failure in Patients Treated with Intensive Vasodilator Therapy," American Journal of Hypertension, Ltd., 1998; 11:1041-1047.
Abstracts—Heart Failure 179A, JACC, Feb. 1999.
Tucker, A. T. et al. Nov. 13, 1999, "Effect of nitric-oxide-generating system on microcirculatory blood flow in skin of patients with severe Raynaud's syndrome: a randomised trial".
Apr. 5, 2005. Supplementary European Search Report from European Patent Application No. 01932915.0.
Cohn et al, The New England Journal of Medicine, 325(5):303-310(1991).
Cohn et al, The New England Journal of Medicine, 314(24):1547-1552(1986).
Carson et al, Circulation, Supplement I, 92(8):I31-I32, Abstract No. 0145(1995).
Francis et al, Circulation, Supplement VI, 87(6):VI40-VI48(1993).
Pierpont et al, Chest, 73(1):8-13(1978).
Massie et al, The American Journal of Cardiology, 40:794-801(1977).
Kaplan et al, Annals of Internal Medicine, 84:639-645(1976).
Bauer et al, Circulation, 84(1):35-39(1991).
The SOLVD Investigators, The New England Journal of Medicine, 327(10):685-691(1992).
Ziesche et al, Circulation, 87(6):VI56-VI64(1993).
Rector et al, Circulation, 87(6):VI71-VI77(1993).
Carson et al, Journal of Cardiac Failure, 5(3):178-187(Sep. 10, 1999).
Dries et al, The New England Journal of Medicine, 340(8):609-616 (Feb. 25, 1999).
Freedman et al, Drugs, 54(Supp. 3):41-50 (1997).
Sherman et al, Cardiologia, 42(2):177-187 (1997).
Biegelson et al, Coronary Artery Disease, 10:241-256 (1999).
Rudd et al, Am. J. Physiol., 277(46):H732-H739 (1999).
Hammerman et al, Am. J. Physiol., 277(46):H1579-H1592 (1999).
Loscalzo et al, Transactions of the American and Climatological Ass., 111:158-163 (2000).
Dupuis, Cardiovascular Drugs and Therapy, 8(3):501-507 (1994).
Dupuis, Cardiovascular Drugs and Therapy, 8(3):501-507 (1994) (Abstract).
von Lutterotti et al, American Journal of Hypertension, 4(4 Part 2):346S-349S (1991).
Burnier et al, Hypertension, 22(3):339-347 (1993).
Johnson, Clinical Pharmacy, vol. 5, pp. 536 and 541 (1986).
Massie et al, Br. Heart J., 45:376-384 (1981).
Turner et al, The American Journal of Cardiology, 47:910-916 (1981)
.
Massie et al, Circulation, 63(3):658-664 (1981).
Nelson et al, Journal of Cardiovascular Pharmacology, 5(4):574-579 (1983).
Leier et al, Circulation, 63(1):102-109 (1981).
Wilson et al, The American Journal of Medicine, 71:627-633 (1981)
.
Biddle et al, J. Clin. Pharmacol., 21:343-350 (1981).
Magorien et al, Clinical Research 27(4) A617 (1979).
Turner et al, Clinical Research, 29(2):246A (1981).
Hibiya et al, Japanese Circulation Journal, 45:966 (Abstract No. 338) (1981).
Kahn, Jonathan, "How a Drug Becomes "Ethnic": Law, Commerce, and the Production of Racial Categories in Medicine," Yale Journal of Heath Policy, Law, and Ethics IV:1 (2004), pp. 1-46.
Parker, John D., et al., "The Effect of Hydralazine on the Development of Tolerance to Continuous Nitroglycerin," The Journal of Pharmacology and Experimental Therapeutics, vol. 280, No. 2, pp. 866-875 1997.
Kalinowski, Leszek, et al., "Race-Specific Differences in Endothelial Function—Predisposition of African Americans to Vascular Diseases," Circulation, Jun. 1, 2004, pp. 2511-2517.

* cited by examiner

US 7,556,824 B2

TRANSDERMAL PATCH COMPOSITION FOR TREATING VASCULAR DISEASES CHARACTERIZED BY NITRIC OXIDE INSUFFICIENCY

RELATED APPLICATIONS

This application is a divisional of U.S. application Ser. No. 09/697,317, filed Oct. 27, 2000, now U.S. Pat. No. 6,635,273, which claims priority to U.S. Provisional Application No. 60/162,230 filed Oct. 29, 1999 and U.S. Provisional Application No. 60/179,020 filed Jan. 31, 2000. This application is related to co-pending U.S. application Ser. No. 10/415,136 filed Apr. 25, 2003, and PCT/US01/14245 filed May 2, 2001.

FIELD OF THE INVENTION

The present invention provides methods of treating and/or preventing vascular diseases characterized by nitric oxide insufficiency by administering a therapeutically effective amount of at least one antioxidant or a pharmaceutically acceptable salt thereof, and at least one of isosorbide dinitrate and isosorbide mononitrate, and, optionally, at least one nitrosated angiotensin-converting enzyme inhibitor, nitrosated beta-adrenergic blocker, nitrosated calcium channel blocker, nitrosated endothelin antagonist, nitrosated angiotensin II receptor antagonist, nitrosated renin inhibitor, and/or at least one compound used to treat cardiovascular diseases. The antioxidant is preferably a hydralazine compound or a pharmaceutically acceptable salt thereof. The present invention also provides methods of treating and/or preventing vascular diseases characterized by nitric oxide insufficiency by administering a therapeutically effective amount of at least one nitrosated angiotensin-converting enzyme inhibitor, nitrosated beta-adrenergic blocker, nitrosated calcium channel blocker, nitrosated endothelin antagonist, nitrosated angiotensin II receptor antagonist and/or nitrosated renin inhibitor, and, optionally, at least one antioxidant and/or at least one compound used to treat cardiovascular diseases. The present invention also provides methods of treating and/or preventing Raynaud's syndrome by administering a therapeutically effective amount of at least one antioxidant or a pharmaceutically acceptable salt thereof, and at least one of isosorbide dinitrate and isosorbide mononitrate, and/or at least one nitrosated angiotensin-converting enzyme inhibitor, nitrosated calcium channel blocker, nitrosated endothelin antagonist, nitrosated angiotensin II receptor antagonist and/or nitrosated renin inhibitor. The present invention also provides novel transdermal patches comprising at least one antioxidant or a pharmaceutically acceptable salt thereof, and at least one of isosorbide dinitrate and isosorbide mononitrate, and/or at least one nitrosated angiotensin-converting enzyme inhibitor, nitrosated beta-adrenergic blocker, nitrosated calcium channel blocker, nitrosated endothelin antagonist, nitrosated angiotensin II receptor antagonist and/or nitrosated renin inhibitor.

BACKGROUND OF THE INVENTION

The decline in cardiovascular morbidity and mortality in the United States over the past three decades has been the result of significant advances in research on cardiovascular disease mechanisms and therapeutic strategies. The incidence and prevalence of myocardial infarction and death from myocardial infarction, as well as that from cerebrovascular accident, have decreased significantly over this period largely owing to advances in prevention, early diagnosis, and treatment of these very common diseases.

Analysis of outcomes by race, however, paints quite a different picture: life expectancy and cardiovascular morbidity rates have improved far less for blacks than whites. Available data show that the likelihood of dying from cardiovascular disease is far greater among black Americans than among white Americans. In this decade, the death rate from cardiovascular disease for black males was 353 per 100,000 population, while that for white males was 244 per 100,000; the rate for black females was 226 per 100,000; while that for white females was 135 per 100,000. Consonant with this important demographic parameter is the observation that there is a higher prevalence of several of the important risk factors for cardiovascular disease, e.g., hypertension, smoking, diabetes mellitus, obesity, and left ventricular hypertrophy, among blacks compared with whites. In addition, outcomes of cardiovascular events are worse for blacks than whites. Following myocardial infarction, blacks have a 50% higher annual mortality rate than whites, and their five year survival is only 70%. Thus, the many advances in cardiovascular medicine that account for the overall improvement in cardiovascular health in the general population have failed to translate into comparable racial benefits.

There is a need in the art for new and more effective compositions and methods for treating vascular diseases. The present invention is directed to these, as well as other, important ends.

SUMMARY OF THE INVENTION

The present invention provides methods for treating and/or preventing vascular diseases characterized by nitric oxide insufficiency by administering to a patient a therapeutically effective amount of at least one antioxidant or a pharmaceutically acceptable salt thereof, and at least one of isosorbide dinitrate and isosorbide mononitrate, and, optionally, at least one nitrosated angiotensin-converting enzyme inhibitor, nitrosated beta-adrenergic blocker, nitrosated calcium channel blocker, nitrosated endothelin antagonist, nitrosated angiotensin II receptor antagonist, nitrosated renin inhibitor, and/or at least one compound used to treat cardiovascular diseases. The antioxidant is preferably a hydralazine compound or a pharmaceutically acceptable salt thereof. The vascular diseases characterized by nitric oxide insufficiency include, for example, hypertension (e.g., low-renin hypertension; salt-sensitive hypertension; low-renin, salt-sensitive hypertension; primary pulmonary hypertension; thromboembolic pulmonary hypertension; pregnancy-induced hypertension; renovascular hypertension), heart failure (e.g., microvascular cardiac ischemia), and left ventricular hypertrophy with disproportionate microvascularization, (i.e., inadequate vascularity) or diastolic dysfunction. The antioxidant and the isosorbide dinitrate or isosorbide mononitrate and optional nitrosated compound and/or compound used to treat cardiovascular diseases can be administered separately or as components of the same composition.

Another aspect of the present invention provides methods for treating and/or preventing vascular diseases characterized by nitric oxide insufficiency by administering to a patient a therapeutically effective amount of at least one nitrosated angiotensin-converting enzyme inhibitor, nitrosated beta-adrenergic blocker, nitrosated calcium channel blocker, nitrosated endothelin antagonist, nitrosated angiotensin II receptor antagonist and/or nitrosated renin inhibitor, and, optionally, at least one antioxidant and/or at least one compound used to treat cardiovascular diseases. The vascular diseases characterized by nitric oxide insufficiency include, for example, hypertension (e.g., low-renin hypertension; salt-sensitive hypertension; low-renin, salt-sensitive hypertension; primary pulmonary hypertension; thromboembolic pulmonary hypertension; pregnancy-induced hypertension; renovascular hypertension), heart failure (e.g., microvascular cardiac ischemia), and left ventricular hypertrophy with disproportionate microvascularization, (i.e., inadequate vascularity) or diastolic dysfunction. The nitrosated compound and optional antioxidant and/or compound used to treat cardiovascular diseases can be administered separately or as components of the same composition.

In another aspect, the present invention provides methods for treating and/or preventing Raynaud's syndrome by administering to a patient a therapeutically effective amount of at least one antioxidant or a pharmaceutically acceptable salt thereof, and at least one of isosorbide dinitrate and isosorbide mononitrate and/or at least one nitrosated angiotensin-converting enzyme inhibitor, nitrosated calcium channel blocker, nitrosated endothelin antagonist, nitrosated angiotensin II receptor antagonist and/or nitrosated renin inhibitor. The antioxidant, isosorbide dinitrate or isosorbide mononitrate, and nitrosated compound can be administered separately or as components of the same composition.

In yet another aspect, the present invention provides novel transdermal patches comprising a therapeutically effective amount of at least one antioxidant at least one of isosorbide dinitrate and isosorbide mononitrate and/or at least one nitrosated angiotensin-converting enzyme inhibitor, nitrosated beta-adrenergic blocker, nitrosated calcium channel blocker, nitrosated endothelin antagonist, nitrosated angiotensin II receptor antagonist and/or nitrosated renin inhibitor, and mixtures thereof.

These and other aspects of the present invention are described in more detail herein.

BRIEF DESCRIPTION OF THE FIGURES

FIG. 2 shows that endothelium-derived NO action is impaired in the forearm microvessels of the black patients compared to the white patients.

DETAILED DESCRIPTION OF THE INVENTION

Figure 1:
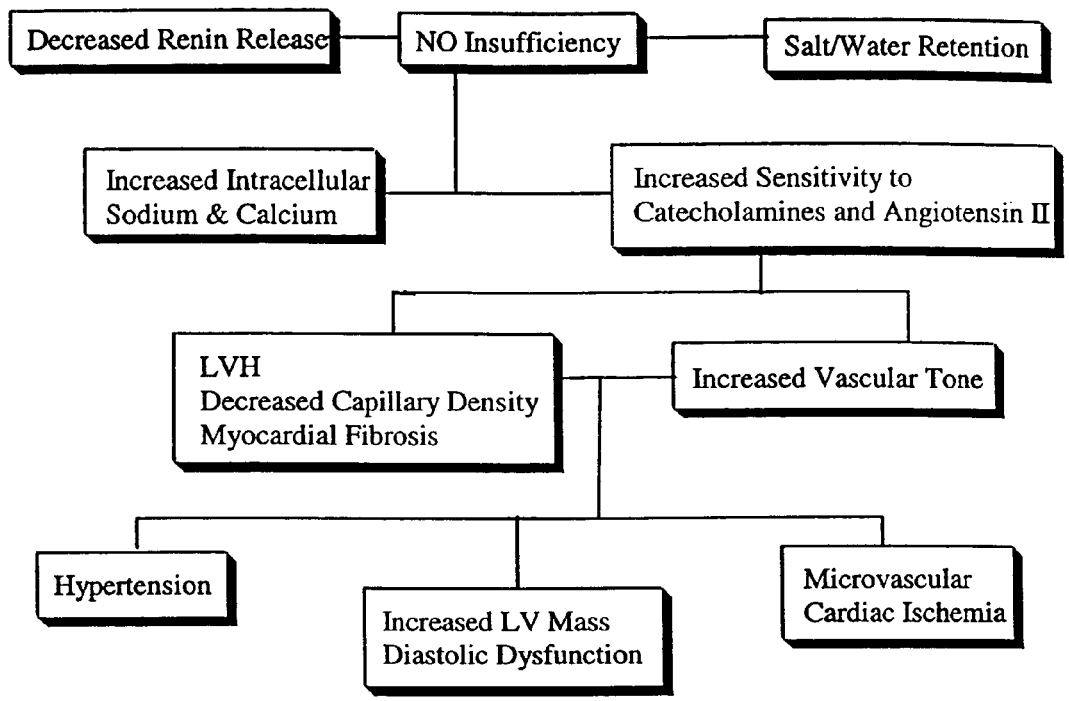
FIG. 1 shows that nitric oxide (NO) insufficiency is associated with increased salt and water retention and a low-renin state. Increased intracellular sodium and calcium in conjunction with reduced NO leads to enhanced sensitivity of vascular smooth muscle cells and cardiomyocytes to the tonic and growth-stimulating properties of catecholamines and angiotensin II. Increased vascular tone, left ventricular hypertrophy with inadequate capillary angiogenesis, and increased matrix production with myocardial fibrosis result. These intermediate phenotypes lead to the clinical disorders of low-renin, salt-sensitive hypertension; disproportionate left ventricular hypertrophy and diastolic dysfunction; and microvascular myocardial ischemia.

As used throughout the disclosure, the following terms, unless otherwise indicated, shall be understood to have the following meanings.

"Patient" refers to animals, preferably mammals, most preferably humans, and includes males and females.

"Therapeutically effective amount" refers to the amount of the compound and/or composition that is effective to achieve its intended purpose.

"Transdermal" refers to the delivery of a compound by passage through the skin and into the blood stream.

"Transmucosal" refers to delivery of a compound by passage of the compound through the mucosal tissue and into the blood stream.

"Penetration enhancement" or "permeation enhancement" refers to an increase in the permeability of the skin or mucosal tissue to a selected pharmacologically active compound such that the rate at which the compound permeates through the skin or mucosal tissue is increased.

"Carriers" or "vehicles" refers to carrier materials suitable for compound administration and include any such material known in the art such as, for example, any liquid, gel, solvent, liquid diluent, solubilizer, or the like, which is non-toxic and which does not interact with any components of the composition in a deleterious manner.

"Hydralazine compound" refers to a compound having the formula:

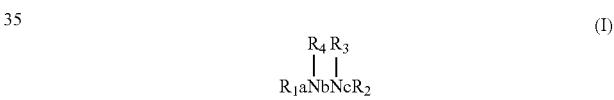

(I)

wherein a, b and c are independently a single or double bond; $R_1$ and $R_2$ are each independently a hydrogen, an alkyl, an ester or a heterocyclic ring; $R_3$ and $R_4$ are each independently a lone pair of electrons or a hydrogen, with the proviso that at least one of $R_1$, $R_2$, $R_3$ and $R_4$ is not a hydrogen. Exemplary hydralazine compounds include budralazine, cadralazine, dihydralazine, endralazine, hydralazine, pildralazine, todralazine, and the like.

"Antioxidant" refers to a compound that can react and quench a free radical.

"Alkyl" refers to a lower alkyl group, a haloalkyl group, a hydroxyalkyl group, an alkenyl group, an alkynyl group, a bridged cycloalkyl group, a cycloalkyl group or a heterocyclic ring, as defined herein.

"Lower alkyl" refers to branched or straight chain acyclic alkyl group comprising one to about ten carbon atoms (preferably one to about eight carbon atoms, more preferably one to about six carbon atoms). Exemplary lower alkyl groups include methyl, ethyl, n-propyl, isopropyl, n-butyl, isobutyl, sec-butyl, t-butyl, pentyl, neopentyl, iso-amyl, hexyl, octyl, and the like.

"Haloalkyl" refers to a lower alkyl group, an alkenyl group, an alkynyl group, a bridged cycloalkyl group, a cycloalkyl group or a heterocyclic ring, as defined herein, to which is appended one or more halogens, as defined herein. Exemplary haloalkyl groups include trifluoromethyl, chloromethyl, 2-bromobutyl, 1-bromo-2-chloro-pentyl, and the like.

"Alkenyl" refers to a branched or straight chain $C_2$-$C_{10}$ hydrocarbon (preferably a $C_2$-$C_8$ hydrocarbon, more preferably a $C_2$-$C_6$ hydrocarbon) which can comprise one or more carbon-carbon double bonds. Exemplary alkenyl groups include propylenyl, buten-1-yl, isobutenyl, penten-1-yl, 2,2-methylbuten-1-yl, 3-methylbuten-1-yl, hexan-1-yl, hepten-1-yl, octen-1-yl, and the like.

"Alkynyl" refers to an unsaturated acyclic $C_2$-$C_{10}$ hydrocarbon (preferably a $C_2$-$C_8$ hydrocarbon, more preferably a $C_2$-$C_6$ hydrocarbon) which can comprise one or more carbon-carbon triple bonds. Exemplary alkynyl groups include ethynyl, propynyl, butyn-1-yl, butyn-2-yl, pentyl-1-yl, pentyl-2-yl, 3-methylbutyn-1-yl, hexyl-1-yl, hexyl-2-yl, hexyl-3-yl, 3,3-dimethyl-butyn-1-yl, and the like.

"Bridged cycloalkyl" refers to two or more cycloalkyl groups, heterocyclic groups, or a combination thereof fused via adjacent or non-adjacent atoms. Bridged cycloalkyl groups can be unsubstituted or substituted with one, two or three substituents independently selected from alkyl, alkoxy, amino, alkylamino, dialkylamino, hydroxy, halo, carboxyl, alkylcarboxylic acid, aryl, amidyl, ester, alkylcarboxylic ester, carboxamido, alkylcarboxamido, oxo and nitro. Exemplary bridged cycloalkyl groups include adamantyl, decahydronapthyl, quinuclidyl, 2,6-dioxabicyclo[3.3.0]octane, 7-oxabycyclo[2.2.1]heptyl, 8-azabicyclo[3,2,1]oct-2-enyl, and the like.

"Cycloalkyl" refers to a saturated or unsaturated cyclic hydrocarbon comprising from about 3 to about 8 carbon atoms. Cycloalkyl groups can be unsubstituted or substituted with one, two or three substituents independently selected from alkyl, alkoxy, amino, alkylamino, dialkylamino, arylamino, diarylamino, alkylarylamino, aryl, amidyl, ester, hydroxy, halo, carboxyl, alkylcarboxylic acid, alkylcarboxylic ester, carboxamido, alkylcarboxamido, oxo and nitro. Exemplary cycloalkyl groups include cyclopropyl, cyclobutyl, cyclopentyl, cyclohexyl, cyclohexenyl, cyclohepta,1,3-dienyl, and the like.

"Heterocyclic ring or group" refers to a saturated or unsaturated cyclic hydrocarbon group having about 2 to about 10 carbon atoms (preferably about 4 to about 6 carbon atoms) where 1 to about 4 carbon atoms are replaced by one or more nitrogen, oxygen and/or sulfur atoms. Sulfur maybe in the thio, sulfinyl or sulfonyl oxidation state. The heterocyclic ring or group can be fused to an aromatic hydrocarbon group. Heterocyclic groups can be unsubstituted or substituted with one, two or three substituents independently selected from alkyl, alkoxy, amino, alkylamino, dialkylamino, arylamino, diarylamino, alkylarylamino, hydroxy, oxo, thial, halo, carboxyl, carboxylic ester, alkylcarboxylic acid, alkylcarboxylic ester, aryl, arylcarboxylic acid, arylcarboxylic ester, alkylcarbonyl, arylcarbonyl, amidyl, ester, carboxamido, alkylcarboxamido, arylcarboxamido, hydrazino, sulfonic acid, sulfonic ester, sulfonamido and nitro. Exemplary heterocyclic groups include pyrrolyl, 3-pyrrolinyl,4,5,6-trihydro-2H-pyranyl, pyridinyl, 1,4-dihydropyridinyl, pyrazolyl, triazolyl, pyrimidinyl, pyridazinyl, oxazolyl, thiazolyl, imidazolyl, indolyl, thiophenyl, furanyl, tetrahydrofuranyl, tetrazolyl, 2-pyrrolinyl, 3-pyrrolinyl, pyrrolindinyl, oxazolindinyl 1,3-dioxolanyl, 2-imidazonlinyl, imidazolindinyl, 2-pyrazolinyl, pyrazolidinyl, isoxazolyl, isothiazolyl, 1,2,3-oxadiazolyl, 1,2,3-triazolyl, 1,3,4-thiadiazolyl, 2H-pyranyl, 4H-pyranyl, piperidinyl, 1,4-dioxanyl, morpholinyl, 1,4-dithianyl, thiomorpholinyl, pyrazinyl, piperazinyl, 1,3,5-triazinyl, 1,3,5-trithianyl, benzo(b)thiophenyl, benzimidazolyl, quinolinyl, and the like.

"Aryl" refers to a monocyclic, bicyclic, carbocyclic or heterocyclic ring system comprising one or two aromatic rings. Exemplary aryl groups include phenyl, pyridyl, napthyl, quinoyl, tetrahydronaphthyl, furanyl, indanyl, indenyl, indoyl, and the like. Aryl groups (including bicyclic aryl groups) can be unsubstituted or substituted with one, two or three substituents independently selected from alkyl, alkoxy, amino, alkylamino, dialkylamino, arylamino, diarylamino, alkylarylamino, hydroxy, carboxyl, carboxylic ester, alkylcarboxylic acid, alkylcarboxylic ester, aryl, arylcarboxylic acid, arylcarboxylic ester, alkylcarbonyl, arylcarbonyl, amidyl, ester, carboxamido, alkylcarboxamido, carbomyl, sulfonic acid, sulfonic ester, sulfonamido and nitro. Exemplary substituted aryl groups include tetrafluorophenyl, pentafluorophenyl, sulfonamide, alkylsulfonyl, arylsulfonyl, and the like.

"Hydroxy" refers to —OH.

"Hydroxyalkyl" refers to a hydroxy group, as defined herein, appended to an alkyl group, as defined herein.

"Alkylcarbonyl" refers to $R_{52}$—C(O)—, wherein $R_{52}$ is an alkyl group, as defined herein.

"Arylcarbonyl" refers to $R_{55}$—C(O)—, wherein $R_{55}$ is an aryl group, as defined herein.

"Ester" refers to $R_{51}$C(O)O— wherein $R_{51}$ is a hydrogen atom, an alkyl group, an aryl group, an alkylaryl group, or an arylheterocyclic ring, as defined herein.

"Alkylaryl" refers to an alkyl group, as defined herein, to which is appended an aryl group, as defined herein. Exemplary alkylaryl groups include benzyl, phenylethyl, hydroxybenzyl, fluorobenzyl, fluorophenylethyl, and the like.

"Arylheterocyclic ring" refers to a bi- or tricyclic ring comprised of an aryl ring, as defined herein, appended via two adjacent carbon atoms of the aryl ring to a heterocyclic ring, as defined herein. Exemplary arylheterocyclic rings include dihydroindole, 1,2,3,4-tetrahydroquinoline, and the like.

"Hydrazino" refers to $H_2N$—N(H)—.

"Compound used to treat cardiovascular diseases" refers to any therapeutic compound, or a pharmaceutically acceptable salt thereof, used to treat any cardiovascular disease. Suitable compounds include, but are not limited to, angiotensin-converting enzyme (ACE) inhibitors (such as, for example, alacepril, benazepril, captopril, ceranapril, cilazapril, delapril, duinapril, enalapril, enalaprilat, fosinopril, imidapril, lisinopril, moveltipril, pentopril, perindopril, quinapril, ramipril, rentipril, spirapril, temocapril, trandolapril, zofenopril, and the like); beta-adrenergic blockers (such as, for example, amosulalol, atenolol, betaxolol, bethanidine, bevantolol, bisoprolol, bopindolol, bufuralol, bunitrolol, bupranolol, butafilolol, carazolol, carteolol, carvedilol, celiprolol, cetamolol, dilevalol, epanolol, indenolol, mepindolol, metipranolol, metoprolol, moprolol, nadolol, nebivolol, nipradilol, penbutolol, pindolol, pronethalol, propranolol, sotalol, sulfinalol, talinolol, tertatolol, tilisolol, timolol, toliprolol, and the like); cholesterol reducers (such as, for example, HMG-CoA reductase inhibitors, including, but not limited to, lovastatin (MEVACOR®), simvastatin (ZOCOR®), pravastatin (PRAVACHOL®), fluvastatin, cerivastatin (BAYCOL®), atorvastatin (LIPITOR®), and the like; sequestrants, including, but not limited to, cholestyramine, colestipol, sialkylaminoalkyl derivatives of cross-linked dextran, and the like; inhibitors of cholesterol absorption, including, but not limited to, beta-sitosterol, acyl CoA-cholersterol acyltransferase inhibitors, melinamide, and the like); calcium channel blockers (such as, for example, amlodipine, aranidipine, barnidipine, benidipine, cilnidipine, clentiazem, diltiazen, efonidipine, fantofarone, felodipine, isradipine, lacidipine, lercanidipine, manidipine, mibefradil, nicardipine, nifedipine, nilvadipine, nisoldipine, nitrendipine, semotiadil, veraparmil, and the like); angiotensin II receptor antagonists (such as, for example, ciclosidomine, eprosartan, furosemide, irbesartan, losartan, saralasin, valsartan, and the like); endothelin antagonists (such as, for example, bosentan, sulfonamide endothelin antagonists, BQ-123, SQ 28608, and the like); renin inhibitors (such as, for example, enalkrein, RO 42-5892, A 65317, CP 80794, ES 1005, ES 8891, SQ 34017, and the like); and mixtures thereof.

"Cardiovascular diseases" refers to any cardiovascular disease, including but not limited to, congestive heart failure, hypertension, pulmonary hypertension, myocardial and cerebral infarctions, atherosclerosis, atherogenesis, thrombosis, ischemic heart disease, post-angioplasty restenosis, coronary artery diseases, renal failure, stable, unstable and variant (Prinzmetal) angina, cardiac edema, renal insufficiency, nephrotic edema, hepatic edema, stroke, and the like.

Two broad classes of cardiovascular disorders are more prevalent among blacks than whites and serve as areas in need of investigative efforts. Hypertension and left ventricular hypertrophy, two related yet independent risk factors for coronary heart disease, are significantly more prevalent among blacks than whites. Blacks also have higher rates of angiographically normal coronary arteries despite a higher prevalence of risk factors for coronary atherosclerosis, and greater morbidity and mortality from coronary heart disease than whites. These paradoxical observations have led some investigators to postulate that blacks harbor a diathesis of the microvasculature that limits perfusion and serves as a stimulus for vascular smooth muscle cell and cardiomyocyte hypertrophy, which, in turn, leads to hypertension and left ventricular hypertrophy, respectively. The underlying basis for this vascular diathesis may involve the endothelium, which has a limited capacity to generate vasodilator and antiproliferative factors or an increased capacity to produce vasoconstrictor and proliferative factors; the vascular smooth muscle cell, which manifests increased sensitivity to vasoconstrictor and proliferative factors; or both, in these individuals.

The present inventors have discovered that a major product of the normal blood vessel that may play a role in the vascular diathesis of blacks is endothelium-derived nitric oxide (NO). Nitric oxide produced by the endothelial cells induces vascular smooth muscle cell relaxation, contributing importantly to resting vascular tone. In addition, NO inhibits vascular smooth muscle cell proliferation and induces apoptosis in smooth muscle cells, which leads to the release of basic fibroblast growth factor and vascular endothelial cell growth factor, in turn supporting endothelial cell proliferation. This sequence of cellular responses is believed to sustain angiogenesis under hypoxic or ischemic conditions.

The role of NO in the vascular diathesis of blacks is illustrated by the consequences of NO insufficiency in the normal responses of the vasculature to NO. Nitric oxide insufficiency suppresses renin release from the juxtaglomerular cells, and induces a sodium chloride/volume sensitive increase in blood pressure. Furthermore, NO insufficiency leads to an increased sensitivity of vascular smooth muscle cells to vasoconstrictors, such as angiotensin II and catecholamines, which amplify the increase in vascular resistance.

Nitric oxide insufficiency promotes vascular smooth muscle cell proliferation following vascular injury, and sustains smooth muscle cell and cardiomyocyte hypertrophy in response to catecholamines and angiotensin II. Furthermore, inadequate NO leads to increased production of extracellular matrix with consequent myocardial fibrosis.

These many cardiovascular responses that result from inadequate NO in the vasculature have clear clinical correlates in the black population. The clinical vascular phenotype of blacks that distinguishes them from whites with similar cardiovascular disorders is one of salt-sensitive, low-renin hypertension; left ventricular hypertrophy disproportionate to afterload and with an inadequate angiogenic response; and microvascular ischemia in the absence of significant epicardial coronary artery disease. The net pathophysiological consequences of these effects are increased peripheral vascular resistance with accompanying arterial hypertension; and an inadequately vascularized, fibrotic increase in left ventricular mass with accompanying diastolic dysfunction and microvascular ischemia.

Given these clinical observations and the role that NO plays in preventing their development, the present inventors have unexpectedly discovered that the principal cardiovascular disorders common among blacks (such as hypertension, left ventricular hypertrophy, and heart failure) result from a specific vascular diathesis that is a direct consequence of nitric oxide insufficiency. An outline of the pathogenic consequences of NO insufficiency that serve as the basis for these cardiovascular disorders is shown in FIG. 1.

NO insufficiency states can be a consequence of reduced synthesis of NO, enhanced inactivation of NO, or both. Possible candidate mechanisms include alterations in the genes that code for endothelial NO synthase or the inducible microvascular and cardiomyocyte NO synthase leading to reduced expression of a normal gene product or appropriate expression of a less active gene product; reduction in the enzymatic activity of NO synthase owing to inadequate cofactor concentrations; or enhanced inactivation of NO by oxidant stress.

Data obtained by the inventors in cultured cells, animal models, and human patients suggest that increased oxidant stress is central to the vascular diathesis of and consequent cardiovascular disorders common among African Americans. Possible candidate mechanisms for the oxidant stress include enhanced production of reactive oxygen species (ROS), decreased antioxidant defenses, or both. The inventors make no a priori assumptions about the temporal or causative relationship between oxidant stress and the vascular phenotype of blacks: oxidant stress may both precede the development of the vascular diathesis and promote its progression once established. Recent data suggest that enhanced ROS production accompanies essential hypertension, atherosclerosis, thrombosis, and diabetes mellitus, and appears in each case, at the very least, to be important in the progression of established disease, if not in its actual genesis.

Endothelium-derived relaxing factor (EDRF), first described by Furchgott et al, *Nature,* 299:373-376 (1980), is an important mediator of vascular function. This endothelial product activates guanylyl cyclase in vascular smooth muscle cells and platelets, leading to vasorelaxation and platelet inhibition, respectively (Loscalzo et al, *Prog Cardiovasc Dis,* 38:87-104 (1995)). The chemical nature of EDRF has been studied using a variety of pharmacological and analytical techniques, and is NO (Ignarro et al, *Circ Res,* 61:866-879 (1987); Palmer et al, *Nature,* 327:524-526 (1987)).

Nitric oxide is synthesized by one of several isoforms of the NO synthase (NOS) family of enzymes, two of which are found in the vasculature, endothelial NOS (eNOS) and inducible NOS (iNOS). eNOS is synthesized by endothelial cells, while iNOS is synthesized by a variety of cell types, including vascular smooth muscle cells, fibroblasts, and (principally microvascular) endothelial cells (Balligand et al, *Am J Physiol,* 268:H1293-1303 (1995)). These enzymes produce NO as a result of the five-electron oxidation of L-arginine to L-citrulline; requisite cofactors include calcium-calmodulin, $O_2$, FAD, FMN, tetrahydrobiopterin thiols, heme, and NADPH. (Moncada et al, *N Engl J Med,* 329:2002-2012 (1993)).

The role of NO in the cardiovascular system has become increasingly apparent over the past fifteen years (Loscalzo et al, *Prog Cardiovasc Dis,* 38:87-104 (1995)). Nitric oxide contributes importantly to resting tone in conductance as well as resistance arteries (Ouyyumi et al, *J Clin Invest,* 95:1747-1755 (1995)), and plays a critical role in the maintenance of peripheral vascular resistance and arterial pressure responses. Inhibition of NOS activity is associated with enhanced vascular sensitivity to vasoconstrictors, such as norepinephrine and angiotensin II (Conrad et al, *Am J Physiol,* 262:R1137-R1144 (1992)), and this effect appears to be mediated, in part, by increased calcium sensitivity (Bank et al, *Hypertension,* 24:322-328 (1994)). Nitric oxide release from the cardiovascular regulatory center in the brain may also be involved in the central regulation of blood pressure, suggesting a role for neuronal NOS in the regulation of vascular tone (Cabrera et al, *Biochem Biophys Res Comm,* 206:77-81 (1995); Mattson et al, *Hypertension,* 28:297-303 (1996)).

Nitric oxide activates renin gene expression in the kidney, and is involved in the baroreceptor-mediated regulation of renin gene expression (Schricker et al, *Pflug Arch,* 428:261-268 (1994)). The dependence of blood pressure on salt intake appears to depend on NO, and NO deficiency states are associated with salt-sensitivity (Tolins et al, *Kidney Internat,* 46:230-236 (1994)). Selective inhibition of iNOS in Dahl R rats has been shown to lead to salt-sensitivity and to the development of salt-dependent hypertension similar to Dahl S rats (Rudd et al, *Am J Physiol,* 277: H732-H739 (1999)). In addition, mice deficient in iNOS (iNOS gene eliminated by targeted disruption) may develop hypertension in response to salt feeding (Rudd et al, *Circulation,* 98:1A (1998)).

Nitric oxide also affects myocardial contractility, and does so both by mediating muscarinic-cholinergic slowing of the heart rate and the contractile response to beta-adrenergic stimulation (Balligand et al, *Proc Nat'l Acad Sci USA,* 90:347-351 (1993)). This latter effect appears to be mediated in vivo through the vagus nerve (Hare et al, *J Clin Invest,* 95:360-366 (1995)).

In both vascular smooth muscle cells and cardiomyocytes, NO inhibits cellular proliferation and limits the proliferative response to growth-promoting substances (Garg et al, *J Clin Invest,* 83:1774-1777 (1986)). Left ventricular hypertrophy tends to occur in adult hearts with inadequate capillary proliferation, and this may account for the microvascular ischemia noted in patients with hypertrophy. Capillary proliferation is generally held to be a rare event in normal adult mammalian hearts. However, recent data from a hypertensive rat model, in which left ventricular hypertrophy commonly occurs, show that treatment with a low-dose of an angiotensin-converting enzyme inhibitor insufficient to prevent hypertension and left ventricular hypertrophy can, nonetheless, evoke capillary angiogenesis. Compared with untreated controls, treatment with the angiotensin converting enzyme inhibitor increased myocardial capillary proliferation (Unger et al, *Hypertension,* 20:478482 (1992)), and this effect was believed to be a consequence of inhibiting the degradation and potentiating the action of bradykinin. Bradykinin increases myocardial blood flow by inducing release of NO from microvascular endothelial cells, and increased blood flow is a powerful stimulus for capillary proliferation (Mall et al, *Bas Res Cardiol,* 85:531-540 (1990)).

Normal metabolic processes in vascular cells are associated with the generation of reactive oxygen intermediates that must be neutralized to limit oxidative damage and cellular dysfunction. In the setting of common cardiovascular disorders or in the presence of common risk factors for atherothrombotic disease, reactive oxygen species (ROS) are generated in abundance, and their rate of synthesis and flux typically exceeds the capacity of endogenous antioxidant mechanisms. Hypercholesterolemia, hyperglycemia (Keaney et al, *Circulation,* 99:189-191 (1999)), cigarette smoking, hyperhomocysteinemia, hypertension, and frank atherosclerosis are all accompanied by an increase in plasma and tissue ROS generation. Superoxide anion, hydrogen peroxide, hydroxyl radical, peroxynitrite, and lipid peroxides all increase in these settings. What remains unknown is whether or not the increase in ROS in these disorder is a primary event, a secondary consequence of the underlying process, or both.

Endogenous antioxidants important for the neutralization (i.e., reduction) of ROS can be categorized into two groups: small-molecule antioxidants and antioxidant enzymes. The former group comprises molecules such as GSH, NADPH, α-tocopherol, vitamin C, and ubiquinol-10; while the latter group comprises the superoxide dismutases, catalase, and glutathione peroxidases. Deficiencies in several of these molecular species have been shown to lead to increased steady-state levels of ROS and vascular dysfunction, including increased platelet activation, arterial thrombosis (Freedman et al, *J Clin Invest,* 97:979-987 (1996); Freedman et al, *Circulation,* 98:1481-1486 (1998)), and reduced production of platelet-derived NO (Kenet et al, *Arterio Thromb Vasc Biol,* 19(8): 2017-2023 (1999)), which is important for limiting expansion of a platelet thrombus (Freedman et al, *Circ Res,* 84:1416-142 (1999)).

ROS generation accompanies the vascular dysfunction associated with several models of atherothrombotic and hypertensive vascular diseases. Hyperhomo-cysteinemic mice (i.e., cystathionine β-synthase knock-out mice) (Eberhardt et al, *Circulation,* 98:144 (1998)), cellular glutathione peroxidase-deficient mice (i.e., cellular glutathione peroxidase knock-out mice), and salt-induced hypertensive rats (i.e., salt-fed Dahl S rats) (Trolliet et al, *Circulation,* 98:1-725 (1998)) all manifest increased vascular ROS, and this increase in ROS is accompanied by reduced NO bioactivity through oxidative inactivation. Endothelial function and NO availability can be improved by improving antioxidant status with a cysteine precursor (Vita et al, *J Clin Invest,* 101:1408-1414 (1998)). In addition, α-tocopherol leads to platelet inhibition (Freedman et al, *Circulation,* 94:2434-2440 (1996)) as one mechanism of its atherothrombotic benefit (Stephens et al, Lancet, 347:781-786 (1996)). The present inventors have also discovered that salt-loading salt-sensitive individuals (Dahl S rats) leads to an approximate 5-fold increase in plasma $F_2$-isoprostanes (8-epi-prostaglandin $F_2$), and this increase precedes the development of florid hypertension. These data all support the role of oxidant stress in the genesis or evolution of vascular dysfunction and disease, and the importance of antioxidant mechanisms in preventing this pathobiology, particularly with regard to African Americans.

In support of the mechanisms illustrated above, minimum forearm vascular resistance is significantly higher among normotensive blacks than whites (Bassett et al, *Am J Hypertension,* 5:781-786 (1992)), and forearm blood-flow responses to isoproterenol are markedly attenuated in normotensive blacks, suggesting a blunted $\beta_2$-vasodilator response in these individuals (Lang et al, *N Engl J Med,* 333:155-160 (1995)). Blacks tend to have greater left ventricular mass than whites for any given level of blood pressure (Koren et al, *Am J Hypertension,* 6:815-823 (1993); Chaturvedi et al, *J Am Coll Cardiol,* 24:1499-1505 (1994)). While not quantitated in any necropsy study, this response is likely to be accompanied by inadequate capillary angiogenesis which, in turn, may account for the diastolic dysfunction and the microvascular ischemia observed in blacks. Interestingly, blacks have been observed to have low levels of urinary kallikrein (Zinner et al, *Am J Epidemiol,* 104:124-132 (1976); Levy et al, *J Clin Invest,* 60:129-138 (1977)), the enzyme responsible for the generation of bradykinin from high-molecular-weight kininogen. Thus, were a similar abnormality in bradykinin and bradykinin-mediated NO production to exist in the coronary vasculature, attenuated blood flow responses may result that would limit capillary angiogenic responses and prevent the endothelial proliferative effects of locally derived NO.

As discovered and described herein, African Americans have a unique vascular diathesis that may serve as the basis for clinically important cardiovascular syndromes. For example, differences in the outcome of left ventricular dysfunction may be a consequence of the enhanced (perhaps salt-dependent) increase in oxidant stress coupled with microvascular endothelial dysfunction and an inadequately vascularized, hypertrophied left ventricle. This constellation of pathophysiological abnormalities may provide the substrate for the important differences in outcome between blacks and whites with left ventricular dysfunction (Dreis et al, *N Engl J Med,* 340:609-616 (1999)). In addition, these observations and their clinical consequences suggest that blacks with abnormal endothelial function and nitric oxide insufficiency states would derive direct and, perhaps, disproportionate clinical benefit from enhancing nitric oxide in the vasculature, either by improving endothelial function, providing exogenous nitric oxide donors, or both.

In view of the above, the present invention provides methods of treating and/or preventing vascular diseases characterized by nitric oxide (NO) insufficiency by administering a therapeutically effective amount of at least one antioxidant or a pharmaceutically acceptable salt thereof, and at least one of isosorbide dinitrate and isosorbide mononitrate, and, optionally, at least one nitrosated angiotensin-converting enzyme inhibitor, nitrosated beta-adrenergic blocker, nitrosated calcium channel blocker, nitrosated endothelin antagonist, nitrosated angiotensin II receptor antagonist, nitrosated renin inhibitor, and/or at least one compound used to treat cardiovascular diseases. For example, the patient can be administered an antioxidant and isosorbide dinitrate, or the patient can be administered an antioxidant and isosorbide mononitrate, or the patient can be administered an antioxidant, isosorbide dinitrate and isosorbide mononitrate. The vascular diseases characterized by NO insufficiency include, for example, hypertension (e.g., low-renin hypertension; salt-sensitive hypertension; low-renin, salt-sensitive hypertension; primary pulmonary hypertension; thromboembolic pulmonary hypertension; pregnancy-induced hypertension; renovascular hypertension), heart failure (e.g., microvascular cardiac ischemia), and left ventricular hypertrophy with disproportionate microvascularization, (i.e., inadequate vascularity) or diastolic dysfunction.

Another aspect of the present invention provides methods for treating and/or preventing vascular diseases characterized by nitric oxide insufficiency by administering to a patient a therapeutically effective amount of at least one nitrosated angiotensin-converting enzyme inhibitor, nitrosated beta-adrenergic blocker, nitrosated calcium channel blocker, nitrosated endothelin antagonist, nitrosated angiotensin II receptor antagonist and/or nitrosated renin inhibitor, and, optionally, at least one antioxidant and/or at least one compound used to treat cardiovascular diseases.

The present invention also provides methods of preventing and treating Raynaud's syndrome by administering a therapeutically effective amount of at least one antioxidant or a pharmaceutically acceptable salt thereof, and at least one of isosorbide dinitrate and isosorbide mononitrate, and, optionally, at least one nitrosated angiotensin-converting enzyme inhibitor, nitrosated calcium channel blocker, nitrosated endothelin antagonist, nitrosated angiotensin II receptor antagonist and/or nitrosated renin inhibitor. For example, the patient can be administered an antioxidant and isosorbide dinitrate, or the patient can be administered an antioxidant and isosorbide mononitrate, or the patient can be administered an antioxidant, isosorbide dinitrate and isosorbide mononitrate. The antioxidant and isosorbide dinitrate or isosorbide mononitrate can be administered separately or as components of the same composition. Raynaud's syndrome is a condition that causes a loss of blood flow to the fingers, toes, nose and/or ears. The affected area turns white from the lack of circulation, then blue and cold, and finally numb. The affected area may also turn red, and may throb, tingle or swell.

Another aspect of the present invention provides novel transdermal patches comprising a therapeutically effective amount of at least one antioxidant and at least one of isosorbide dinitrate and isosorbide mononitrate and/or at least one nitrosated angiotensin-converting enzyme inhibitor, nitrosated beta-adrenergic blocker, nitrosated calcium channel blocker, nitrosated endothelin antagonist, nitrosated angiotensin II receptor antagonist, nitrosated renin inhibitor, and mixtures thereof.

In the present invention, the antioxidants include small-molecule antioxidants and antioxidant enzymes. Suitable small-molecule antioxidants include, but are not limited to, hydralazine compounds, glutathione, vitamin C, vitamin E, cysteine, N-acetyl-cysteine, β-carotene, ubiquinone, ubiquinol-10, tocopherols, coenzyme Q, and the like. Suitable antioxidant enzymes include, but are not limited to, superoxide dismutase, catalase, glutathione peroxidase, and the like. Suitable antioxidants are described more fully in the literature, such as in Goodman and Gilman, The Pharmacological Basis of Therapeutics (9th Edition), McGraw-Hill, 1995; and the Merck Index on CD-ROM, Twelfth Edition, Version 12:1, 1996; and on STN Express, file phar and file reg.

The preferred antioxidant is a hydralazine compound that is preferably administered in the form of a pharmaceutically acceptable salt; more preferably in the form of hydralazine hydrochloride. Hydralazine hydrochloride is commercially available from, for example, Lederle Standard Products (Pearl River, N.Y.), and Par Pharmaceuticals Inc. (Spring Valley, N.Y.).

Isosorbide dinitrate is commercially available, for example, under the trade names DILATRATE®-SR (Schwarz Pharma, Milwaukee, Wis.); ISORDIL® and ISORDILR TITRADOSE® (Wyeth Laboratories Inc., Philadelphia, Pa.); and SORBITRATE® (Zeneca Pharmaceuticals, Wilmington, Del.).

Isosorbide mononitrate is commercially available, for example, under the trade names IMDUR® (A. B. Astra, Sweden); MONOKET® (Schwarz Pharma, Milwaukee, Wis.); and ISMO® (Wyeth-Ayerst company, Philadelphia, Pa.).

The nitrosated angiotensin-converting enzyme inhibitors, nitrosated beta-adrenergic blockers, nitrosated calcium channel blockers, nitrosated endothelin antagonists, nitrosated angiotensin II receptor antagonists and nitrosated renin inhibitors of the present invention include any known angiotensin-converting enzyme inhibitors, beta-adrenergic blockers, calcium channel blockers, endothelin antagonists, angiotensin II receptor antagonists and renin inhibitors that have been nitrosated through one or more sites such as oxygen (hydroxyl condensation), sulfur (sulfhydryl condensation), and/or nitrogen. The nitrosated compounds of the present invention can be prepared using conventional methods known to one skilled in the art. For example, known methods for nitrosating compounds are described in U.S. Pat. Nos. 5,380, 758 and 5,703,073; WO 97/27749; WO 98/19672; and Oae et al, *Org. Prep. Proc. Int.*, 15(3):165-198 (1983), the disclosures of each of which are incorporated by reference herein in their entirety. WO 98/21193 discloses nitrosated ACE inhibitors and nitrosated beta-adrenergic blockers, the disclosure of which is incorporated by reference herein in its entirety. WO 99/00361 discloses nitrate salts of ACE inhibitors, the disclosure of which is incorporated by reference herein in its entirety.

Suitable angiotensin-converting enzyme inhibitors, include, but are not limited to, alacepril, benazepril, captopril, ceranapril, cilazapril, delapril, duinapril, enalapril, enalaprilat, fosinopril, imidapril, lisinopril, moveltipril, pentopril, perindopril, quinapril, ramipril, rentipril, spirapril, temocapril, trandolapril, zofenopril, and the like. Suitable angiotensin-converting enzyme inhibitors are described more fully in the literature, such as in Goodman and Gilman, The Pharmacological Basis of Therapeutics (9th Edition), McGraw-Hill, 1995; and the Merck Index on CD-ROM, Twelfth Edition, Version 12:1, 1996; and on STN Express, file phar and file registry.

Suitable beta-adrenergic blockers, include, but are not limited to, amosulalol, atenolol, betaxolol, bethanidine, bevantolol, bisoprolol, bopindolol, bufuralol, bunitrolol, bupranolol, butafilolol, carazolol, carteolol, carvedilol, celiprolol, cetamolol, dilevalol, epanolol, indenolol, mepindolol, metipranolol, metoprolol, moprolol, nadolol, nebivolol, nipradilol, penbutolol, pindolol, pronethalol, propranolol, sotalol, sulfinalol, talinolol, tertatolol, tilisolol, timolol, toliprolol, and the like. Suitable beta-adrenergic blockers are described more fully in the literature, such as in Goodman and Gilman, The Pharmacological Basis of Therapeutics (9th Edition), McGraw-Hill, 1995; and the Merck Index on CD-ROM, Twelfth Edition, Version 12:1, 1996; and on STN Express, file phar and file registry.

Suitable calcium channel blockers, include, but are not limited to, amlodipine, aranidipine, barnidipine, benidipine, cilnidipine, clentiazem, diltiazen, efonidipine, fantofarone, felodipine, isradipine, lacidipine, lercanidipine, manidipine, mibefradil, nicardipine, nifedipine, nilvadipine, nisoldipine, nitrendipine, semotiadil, veraparmil, and the like. Suitable calcium channel blockers are described more fully in the literature, such as in Goodman and Gilman, The Pharmacological Basis of Therapeutics (9th Edition), McGraw-Hill, 1995; and the Merck Index on CD-ROM, Twelfth Edition, Version 12:1, 1996; and on STN Express, file phar and file registry.

Suitable endothelin antagonists, include, but are not limited to, bosentan, sulfonamide endothelin antagonists, BQ-123, SQ 28608, and the like. Suitable endothelin antagonists are described more fully in the literature, such as in Goodman and Gilman, The Pharmacological Basis of Therapeutics (9th Edition), McGraw-Hill, 1995; and the Merck Index on CD-ROM, Twelfth Edition, Version 12:1, 1996; and on STN Express, file phar and file registry.

Suitable angiotensin II receptor antagonists, include, but are not limited to, ciclosidomine, eprosartan, furosemide, irbesartan, losartan, saralasin, valsartan, and the like. Suitable angiotensin II receptor antagonists are described more fully in the literature, such as in Goodman and Gilman, The Pharmacological Basis of Therapeutics (9th Edition), McGraw-Hill, 1995; and the Merck Index on CD-ROM, Twelfth Edition, Version 12:1, 1996; and on STN Express, file phar and file registry.

Suitable renin inhibitors, include, but are not limited to, enalkrein, RO 42-5892, A 65317, CP 80794, ES 1005, ES 8891, SQ 34017, and the like). Suitable renin inhibitors are described more fully in the literature, such as in Goodman and Gilman, The Pharmacological Basis of Therapeutics (9th Edition), McGraw-Hill, 1995; and the Merck Index on CD-ROM, Twelfth Edition, Version 12:1, 1996; and on STN Express, file phar and file registry.

In the methods of the invention, the antioxidant and at least one of isosorbide dinitrate and isosorbide mononitrate, and, optionally, at least one nitrosated compound, and/or compound used to treat cardiovascular diseases can be administered as separate components or as components of the same composition. When the antioxidant and at least one of isosorbide dinitrate and isosorbide mononitrate are administered as separate components for the treatment of vascular diseases characterized by NO insufficiency or Raynaud's syndrome, they are preferably administered to the patient at about the same time. "About the same time" means that within about thirty minutes of administering one compound (e.g., antioxidant or isosorbide dinitrate or isosorbide mononitrate) to the patient, the other compound (e.g., isosorbide dinitrate or isosorbide mononitrate or antioxidant) is administered to the patient. "About the same time" also includes simultaneous administration of the compounds.

In addition to the administration of the combination of the antioxidant and isosorbide dinitrate or isosorbide mononitrate for the treatment of vascular diseases characterized by NO insufficiency, the patients can receive digitalis such as digoxin and/or diuretics and/or at least one nitrosated angiotensin-converting enzyme inhibitor, nitrosated beta-adrenergic blocker, nitrosated calcium channel blocker, nitrosated endothelin antagonist, angiotensin II receptor antagonist, nitrosated renin inhibitor, and/or at least one compound used to treat cardiovascular diseases.

The digoxin is preferably administered orally to achieve a steady state blood serum concentration of at least about 0.7 nanograms per ml to about 2.0 nanograms per ml. The diuretic is administered, preferably orally, to manage edema. Suitable diuretics include, but are not limited to, thiazides (such as, for example, chlorothiazide, hydrochlorothiazide); ethacrynic acid, furosemide, spironalactone, triamterene or mixtures thereof. Depending on the diuretic used, potassium may also be administered to the patient in order to optimize the fluid balance while avoiding hypokalemic alkalosis. The administration of potassium can be in the form of potassium chloride or by the daily ingestion of foods with high potassium content such as, for example, bananas, orange juice, and the like. The method of administration of these compounds is described in further detail in U.S. Pat. No. 4,868,179, the disclosure of which is incorporated by reference herein in its entirety.

The compounds and compositions of the invention can be administered by any available and effective delivery system including, but not limited to, orally, bucally, parenterally, by inhalation spray, topically (including transdermally), or rectally in dosage unit formulations containing conventional nontoxic pharmaceutically acceptable carriers, adjuvants, and vehicles as desired. The preferred methods of administration are by oral administration or topical application (transdermal application).

Topical administration can also involve the use of transdermal administration such as transdermal patches or iontophoresis devices. Dosage forms for topical administration of the compounds and compositions can include creams, sprays, lotions, gels, ointments, and the like. In such dosage forms, the compositions of the invention can be mixed to form white, smooth, homogeneous, opaque cream or lotion with, for example, benzyl alcohol 1% or 2% (wt/wt) as a preservative, emulsifying wax, glycerin, isopropyl palmitate, lactic acid, purified water and sorbitol solution. In addition, the compositions can contain polyethylene glycol 400. They can be mixed to form ointments with, for example, benzyl alcohol 2% (wt/wt) as preservative, white petrolatum, emulsifying wax, and tenox II (butylated hydroxyanisole, propyl gallate, citric acid, propylene glycol). Woven pads or rolls of bandaging material, e.g., gauze, can be impregnated with the compositions in solution, lotion, cream, ointment or other such form can also be used for topical application.

The compositions can also be applied topically using a transdermal system, such as one of an acrylic-based polymer adhesive with a resinous crosslinking agent impregnated with the composition and laminated to an impermeable backing. In a preferred embodiment, the compositions of the present invention are administered in the form of a transdermal patch, more preferably in the form of a sustained-release transdermal patch. The transdermal patches of the present invention can include any conventional form such as, for example, adhesive matrix, polymeric matrix, reservoir patch, matrix or monolithic-type laminated structure, and are generally comprised of one or more backing layers, adhesives, penetration enhancers, an optional rate controlling membrane and a release liner which is removed to expose the adhesives prior to application. Polymeric matrix patches also comprise a polymeric-matrix forming material. Suitable transdermal patches are described in more detail in, for example, U.S. Pat. Nos. 5,262,165, 5,948,433, 6,010,715 and 6,071,531, the disclosure of each of which are incorporated herein in their entirety.

Solid dosage forms for oral administration can include capsules, sustained-release capsules, tablets, chewable tablets, sublingual tablets, effervescent tablets, pills, powders, granules and gels. In such solid dosage forms, the active compounds can be admixed with at least one inert diluent, such as sucrose, lactose or starch. Such dosage forms can also comprise, as is normal practice, additional substances other than inert diluents, e.g., lubricating agents, such as magnesium stearate. In the case of capsules, tablets, effervescent tablets, and pills, the dosage forms can also comprise buffering agents. Soft gelatin capsules can be prepared to contain a mixture of the active compound or composition and vegetable oil. Hard gelatin capsules can contain granules of the active compound in combination with a solid, pulverulent carrier, such as lactose, saccharose, sorbitol, mannitol, potato starch, corn starch, amylopectin, or cellulose derivatives of gelatin. Tablets and pills can be prepared with enteric coatings.

Liquid dosage forms for oral administration can include pharmaceutically acceptable emulsions, solutions, suspensions, syrups, and elixirs containing inert diluents commonly used in the art, such as water. Such compositions can also comprise adjuvants, such as wetting agents, emulsifying and suspending agents, and sweetening, flavoring, and perfuming agents.

Suppositories for rectal administration of the compounds or compositions can be prepared by mixing the drug with a suitable nonirritating excipient such as cocoa butter and polyethylene glycols which are solid at room temperature but liquid at rectal temperature, such that they will melt in the rectum and release the drug.

The term parenteral includes subcutaneous injections, intravenous, intramuscular, intrasternal injection, or infusion techniques. Injectable preparations, for example, sterile injectable aqueous or oleaginous suspensions can be formulated according to the known art using suitable dispersing agents, wetting agents and/or suspending agents. The sterile injectable preparation can also be a sterile injectable solution or suspension in a nontoxic parenterally acceptable diluent or solvent, for example, as a solution in 1,3-butanediol. Among the acceptable vehicles and solvents that can be used are water, Ringer's solution, and isotonic sodium chloride solution. Sterile fixed oils are also conventionally used as a solvent or suspending medium.

The compounds and compositions of the invention will typically be administered in a pharmaceutical composition comprising one or more carriers or excipients. Examples of suitable carriers include, for example, water, silicone, waxes, petroleum jelly, polyethylene glycols, propylene glycols, liposomes, sugars, salt solutions, alcohol, vegetable oils, gelatins, lactose, amylose, magnesium stearate, talc, surfactants, silicic acids, viscous paraffins, perfume oils, fatty acid monoglycerides and diglycerides, petroethral fatty acid esters, hydroxymethylcelluloses, polyvinyl-pyrrolidones, and the like. The pharmaceutical preparations can be sterilized and if desired, mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously react with the active compounds. For topical application, the compositions can also include one or more permeation enhancers including, for example, dimethylsulfoxide (DMSO), dimethyl formamide (DMF), N,N-dimethylacetamide (DMA), decylmethylsulfoxide (C10MSO), polyethylene glycol monolaurate (PEGML), glyceral monolaurate, lecithin, 1-substituted azacycloheptan-2-ones, particularly 1-N-dodecylcyclazacycoheptan-2-ones (available under the trademark AZONE from Nelson Research & Development Co., Irvine Calif.), alcohols and the like. For parenteral application, particularly suitable vehicles consist of solutions, preferably oily or aqueous solutions, as well as suspensions, emulsions, or implants. Aqueous suspensions can contain substances which increase the viscosity of the suspension and include, for example, sodium carboxymethyl cellulose, sorbitol and/or dextran. Optionally, the suspension can contain stabilizers. The compositions, if desired, can also contain minor amounts of wetting agents, emulsifying agents and/or pH buffering agents.

Various delivery systems are known and can be used to administer the compounds or compositions of the present invention, including, for example, encapsulation in liposomes, microbubbles, emulsions, microparticles, microcapsules and the like. The required dosage can be administered as a single unit or in a sustained release form.

While individual needs may vary, determination of optimal ranges for effective amounts of the compounds and/or compositions is within the skill of the art and can be determined by standard clinical techniques, including reference to Goodman and Gilman, supra; The Physician's Desk Reference, Medical Economics Company, Inc., Oradell, N.J., 1995; and Drug Facts and Comparisons, Inc., St. Louis, Mo., 1993. Generally, the dosage required to provide an effective amount of the compounds and compositions, which can be adjusted by one of ordinary skill in the art, will vary depending on the age, health, physical condition, sex, diet, weight, extent of the dysfunction of the recipient, frequency of treatment and the nature and scope of the dysfunction or disease, medical condition of the patient, the route of administration, pharmacological considerations such as the activity, efficacy, pharmacokinetic and toxicology profiles of the particular compound used, whether a drug delivery system is used, and whether the compound is administered as part of a drug combination.

The compounds and compositions of the present invention can be formulated as pharmaceutically acceptable salts. Pharmaceutically acceptable salts include, for example, alkali metal salts and addition salts of free acids or free bases. The nature of the salt is not critical, provided that it is pharmaceutically-acceptable. Suitable pharmaceutically-acceptable acid addition salts may be prepared from an inorganic acid or from an organic acid. Examples of such inorganic acids include, but are not limited to, hydrochloric, hydrobromic, hydroiodic, nitric, carbonic, sulfuric and phosphoric acid and the like. Appropriate organic acids include, but are not limited to, aliphatic, cycloaliphatic, aromatic, heterocyclic, carboxylic and sulfonic classes of organic acids, such as, for example, formic, acetic, propionic, succinic, glycolic, gluconic, lactic, malic, tartaric, citric, ascorbic, glucuronic, maleic, fumaric, pyruvic, aspartic, glutamic, benzoic, anthranilic, mesylic, salicylic, p-hydroxybenzoic, phenylacetic, mandelic, embonic (pamoic), methanesulfonic, ethanesulfonic, benzenesulfonic, pantothenic, toluenesulfonic, 2-hydroxyethanesulfonic, sulfanilic, stearic, algenic, β-hydroxybutyric, cyclohexylaminosulfonic, galactaric and galacturonic acid and the like. Suitable pharmaceutically-acceptable base addition salts include, but are not limited to, metallic salts made from aluminum, calcium, lithium, magnesium, potassium, sodium and zinc or organic salts made from primary, secondary and tertiary amines, cyclic amines, N,N'-dibenzylethylenediamine, chloroprocaine, choline, diethanolamine, ethylenediamine, meglumine (N-methylglucamine) and procaine and the like. All of these salts may be prepared by conventional means from the corresponding compound by reacting, for example, the appropriate acid or base with the compound.

In preferred embodiments, the hydralazine is administered in an amount of about 30 milligrams per day to about 300 milligrams per day; the isosorbide dinitrate is administered in an amount of about 20 milligrams per day to about 200 milligrams per day; and the isosorbide mononitrate is administered in an amount of about 10 milligrams per day to about 120 milligrams per day. The preferred amounts of hydralazine and/or isosorbide dinitrate or isosorbide mononitrate can be administered as a single dose once a day; in multiple doses several times throughout the day; or in a sustained-release formulation.

The present invention also provides pharmaceutical kits comprising one or more containers filled with one or more of the ingredients of the pharmaceutical compounds and/or compositions. Such kits can also include, for example, other compounds and/or compositions (e.g., diuretics, digoxin, nitrosated compounds, compounds used to treat cardiovascular diseases and the like), a device(s) for administering the compounds and/or compositions, and written instructions in a form prescribed by a governmental agency regulating the manufacture, use or sale of pharmaceuticals or biological products, which instructions can also reflects approval by the agency of manufacture, use or sale for human administration.

EXAMPLES

The following examples are for purposes of illustration only, and are not intended to limit the scope of the specification or claims.

Example 1

Figure 2:
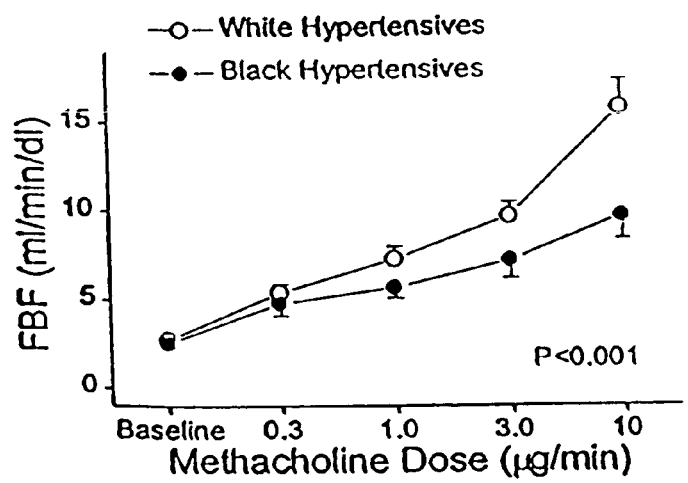
FIG. 2 shows forearm blood flow responses to intra-arterial methacholine that were assessed using venous occlusion plethysmography in 20 white and 16 black patients with a clinical history of hypertension (BP>140/90).

As described herein, NO deficiency is a central pathophysiologic mechanism for the black vascular diathesis. To examine this issue in forearm microvessels, the vasodilator responses to intra-arterial infusions of methacholine, sodium nitroprusside, and verapamil were examined using venous occlusion plethysmography in 36 white and black hypertensive patients. These patients had no other coronary factors, such as smoking, diabetes mellitus, or hypercholesterolemia, and the two groups were matched in terms of age, gender, lipid levels, blood pressure, and anti-hypertensive treatment. Similar to previous reports (Lang et al, *N Engl J Med,* 333: 155-160 (1995); Panza et al, *N Engl J Med,* 323:22-27 (1990)), the dilator response to methacholine, but not nitroprusside, was significantly reduced in these hypertensive patients compared to age-matched normotensive controls (Sherman et al, *Circulation,* 98:1-376 (1998)). Regarding racial differences, as shown in FIG. 2, vasodilation in response to methacholine was markedly worse in the black hypertensive patients compared to white hypertensive patients. There were no racial differences in the responses to sodium nitroprusside or verapamil (data not shown), suggesting that this impairment of NO action in black hypertensives is at the endothelial level and that dysfunction of vascular smooth muscle does not account for the impaired response. These findings have important implications for the pathogenesis of hypertension and myocardial ischemia.

Example 2

Figure 3A:
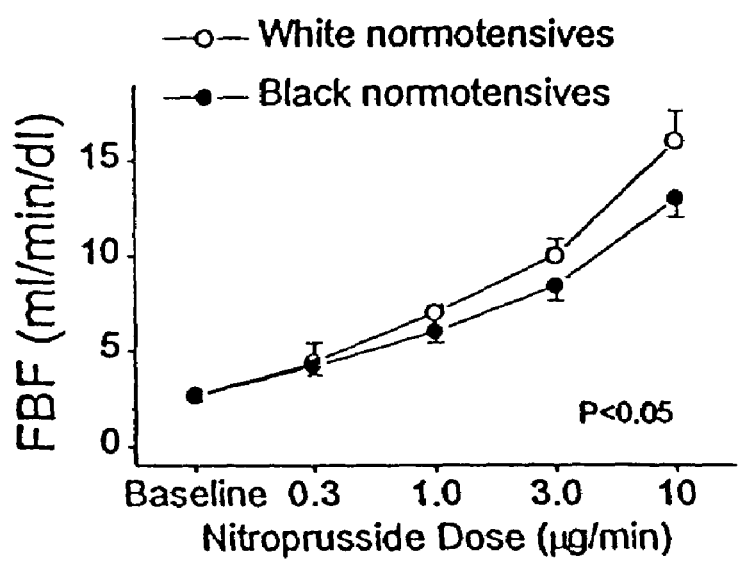
FIGS. 3A and 3B show forearm blood flow responses to nitroprusside (FIG. 3A) and methacholine (FIG. 3B) that were assessed by venous occlusion plethysmography in 25 white and 21 black patients without hypertension. The dilator response to sodium nitroprusside (FIG. 3A) was significantly lower in black patients, while there was no racial difference in response to methacholine (FIG. 3B).
Figure 3B:
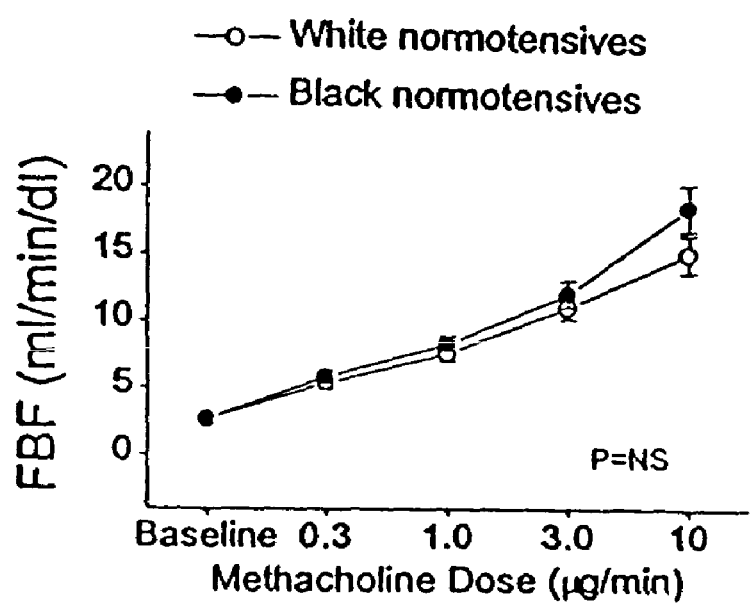

To investigate the issue of whether NO deficiency is a primary or secondary phenomenon in hypertensive black patients, 46 normotensive white and black patients who were matched for age and gender were compared. As shown in FIG. 3B, the vasodilator responses to methacholine were not significantly different in black and white normotensive patients. However, the response to sodium nitroprusside (FIG. 3A) was significantly lower in the black normotensive patients. This finding shows that there is an impairment in the vasodilator response exogenous source of NO in black patients even prior to the development of hypertension, an observation that would be consistent with a primary rather than secondary role in the black vascular diathesis. These findings are consistent with recently published results by other investigators (Lang et al, *N Engl J Med,* 333:155-160 (1995); Cardillo et al, *Hypertension* 31:1235-1239 (1998)).

Example 3

Figure 4A:
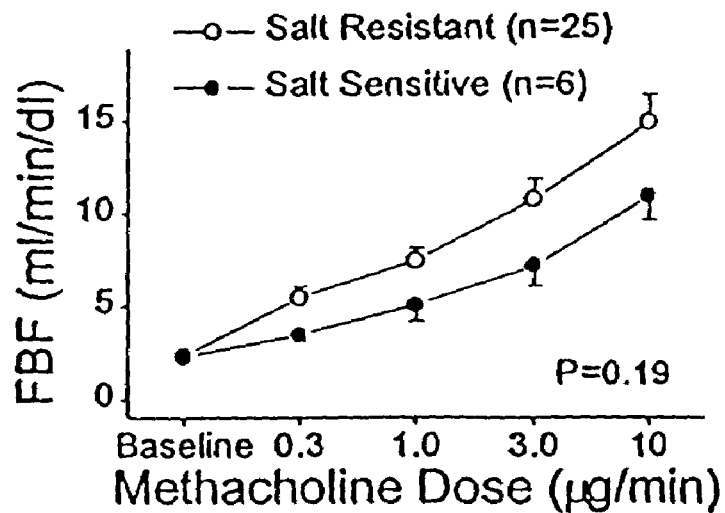
FIGS. 4A and 4B show the effect of salt-sensitivity on forearm microvascular function. By repeated measures ANOVA, there were trends for impaired responses to methacholine (FIG. 4A) and sodium nitroprusside (FIG. 4B) in salt-sensitive black patients.
Figure 4B:
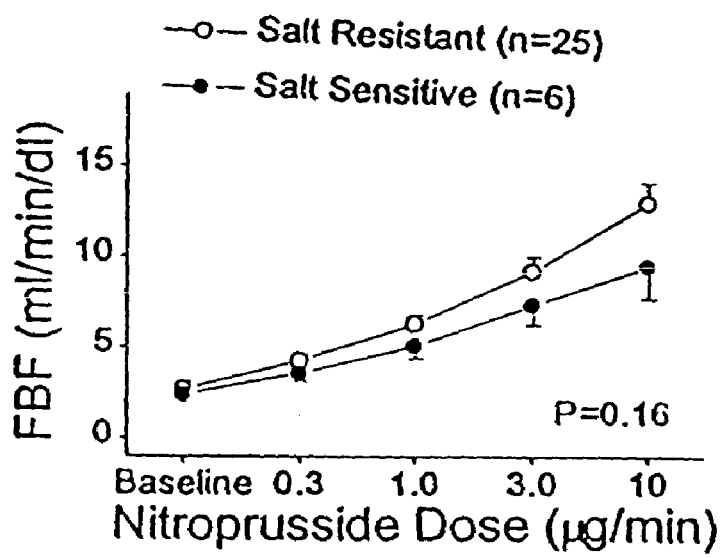

Black patients have a preponderance of salt-sensitive hypertension, and the data described herein show that NO deficiency is a pathogenic mechanism of salt-sensitive hypertension in experimental models (Rudd et al, *Am J Physiol,* 277: H732-H739 (1999)). To explore the relation between salt-sensitivity and endothelium-derived NO action in black patients prior to the development of hypertension, the blood pressure response to salt-loading and salt-deprivation using an established inpatient protocol (Weinberger et al, *Hypertension,* 8:II-127-II-134 (1986)) in a group of normotensive black patients was assessed. Briefly, blood pressure was continuously monitored non-invasively during a salt load (sodium 458 mEq over 24 hours) and during a period of salt depletion (furosemide treatment and sodium intake 10 mEq over 24 hours). Patients were considered to be salt-sensitive if mean blood pressure was at least 10 mm Hg higher during the salt loading period (Weinberger et al, *Hypertension,* 8:II-127-II-134 (1986)). As shown in FIGS. 4A-B, there were trends for impaired vasodilator responses to both methacholine (FIG. 4A) and sodium nitroprusside (FIG. 4B). The vasodilator responses to verapamil were equivalent in salt-sensitive and salt-resistant patients (data not shown). These data show impaired NO action in the microvasculature of salt sensitive individuals prior to the development of hypertension.

Example 4

The effects of hypertension and race on conduit vessel function were examined using a well-established brachial ultrasound technique (Vita et al, Lanzer & Lipton, Eds., *Diagnostics of Vascular Diseases: Principles and Technology*. Berlin:Springer-Verlag, pp. 249-259 (1996)) in 370 patients (178 black, 192 white). As shown in Table 1, there were no significant differences in flow-mediated dilation or nitroglycerin-mediated dilation according to race. However, hypertension was associated with a highly significant reduction in both flow-mediated dilation and nitroglycerin-mediated dilation. Further, systolic blood pressure was inversely correlated with flow-mediated dilation ($r=-0.30$, $P<0.001$) and nitroglycerin-mediated dilation ($r=-0.33$, $P<0.001$). Diastolic pressure correlated to a similar extent with vascular function. By multiple linear regression analysis, vessel size and systolic blood pressure were the only independent predictors of flow-mediated dilation in this sizable group of patients. Thus, both black and white patients with hypertension demonstrate a significant impairment of NO action in conduit arteries (Gokce et al, *Circulation*, 99(25) 3234-3240 (1999)).

TABLE 1

| Conduit Vasomotor Function By Race | | | |
|---|---|---|---|
| | White Patients | Black Patients | P |
| FMD (%) | | | |
| Normotensive | 11.5 ± 5.9 | 13.3 ± 7.2 | NS |
| Hypertensive | 9.5 ± 5.3* | 8.8 ± 6.2* | NS |
| NTG-response (%) | | | |
| Normotensive | 18.1 ± 8.1 | 20.6 ± 8.4 | NS |
| Hypertensive | 14.6 ± 6.2* | 16.4 ± 7.1* | NS |

Data are mean ± SD.
*$p < 0.001$ compared to race matched normotensives.

Each of the above examples demonstrate that NO action is impaired in the microvasculature of black hypertensive patients to a greater extent than in white hypertensive patients. There is a suggestion that this abnormality may precede the development of hypertension, particularly in salt-sensitive individuals, consistent with a pathogenic role. In conduit vessels, a marked impairment of NO action that may contribute to ischemic heart disease and stroke has been demonstrated. This abnormality appears to be independent of race, a finding that is consistent with possibility that the impairment is a consequence of blood pressure elevation of any cause. Since African Americans have a greater incidence of hypertension and a preponderance of salt-sensitive hypertension, these findings lend further support to the hypothesis that NO insufficiency contributes to the pathogenesis of ischemic heart disease in this population.

The disclosure of each patent, patent application and publication cited herein is hereby incorporated by reference herein in its entirety.

Although the invention has been set forth in detail, one skilled in the art will appreciate that numerous changes and modifications can be made to the invention without departing from the spirit and scope thereof.

What is claimed is:

1. A transdermal patch comprising a therapeutically effective amount of a hydralazine compound of formula I and at least one of isosorbide dinitrate and isosorbide mononitrate, wherein the isosorbide dinitrate is present in an amount to deliver about 20 milligrams per day to about 200 milligrams per day and/or the isosorbide mononitrate is present in an amount to deliver about 10 milligrams per day to about 120 milligrams per day; wherein the hydralazine compound of formula (I) is:

wherein a, b and c are independently a single or double bond; $R_1$ and $R_2$ are each independently a hydrogen, an alkyl, an ester or a heterocyclic ring; $R_3$ and $R_4$ are each independently a lone pair of electrons or a hydrogen; with the proviso that at least one of $R_1$, $R_2$, $R_3$ and $R_4$ is not a hydrogen.

2. The transdermal patch of claim 1, further comprising a pharmaceutically acceptable carrier.

3. The transdermal patch of claim 1, wherein the hydralazine compound is budralazine, cadralazine, dihydralazine, endralazine, hydralazine hydrochloride, pildralazine or todralazine or a pharmaceutically acceptable salt thereof.

4. The transdermal patch of claim 3, wherein the at least one hydralazine compound is hydralazine hydrochloride.

5. The transdermal patch of claim 4, wherein the hydralazine hydrochloride is present in an amount to deliver about 30 milligrams to about 300 milligrams per day.

6. The transdermal patch of claim 4, comprising hydralazine hydrochloride and isosorbide dinitrate.

7. The transdermal patch of claim 4, comprising hydralazine hydrochloride and isosorbide mononitrate.

8. The transdermal patch of claim 1, wherein the transdermal patch is a sustained-release transdermal patch.

* * * * *